(12) United States Patent
Asselin et al.

(10) Patent No.: US 11,456,165 B2
(45) Date of Patent: Sep. 27, 2022

(54) SPATIO-TEMPORAL LOCALIZATION FOR MASS SPECTROMETRY SAMPLE ANALYSIS

(71) Applicant: Queen's University at Kingston, Kingston (CA)

(72) Inventors: Mark Asselin, Kingston (CA); Gabor Fichtinger, Kingston (CA)

(73) Assignee: Queen's University at Kingston, Kingston (CA)

(*) Notice: Subject to any disclaimer, the term of this patent is extended or adjusted under 35 U.S.C. 154(b) by 335 days.

(21) Appl. No.: 16/906,045

(22) Filed: Jun. 19, 2020

(65) Prior Publication Data

US 2020/0402787 A1  Dec. 24, 2020

Related U.S. Application Data

(60) Provisional application No. 62/864,137, filed on Jun. 20, 2019.

(51) Int. Cl.
*H01J 49/16* (2006.01)
*H01J 49/00* (2006.01)
(Continued)

(52) U.S. Cl.
CPC .......... *H01J 49/16* (2013.01); *A61B 5/14546* (2013.01); *H01J 49/00* (2013.01);
(Continued)

(58) Field of Classification Search
CPC .......... H01J 49/16; H01J 49/164; H01J 49/00; H01J 49/0004; A61B 5/14546; A61B 2018/00607; A61B 2018/00773
(Continued)

(56) References Cited

U.S. PATENT DOCUMENTS

| 10,397,355 B2 * | 8/2019 | Hajj ........................ H04L 67/12 |
| 2016/0054180 A1 * | 2/2016 | Giusfredi .............. G01J 3/0205 |
| | | 250/339.07 |
| 2022/0051887 A1 * | 2/2022 | Dziekonski ........... H01J 49/426 |

FOREIGN PATENT DOCUMENTS

WO   WO2017/182794 A1   10/2017

OTHER PUBLICATIONS

Balog J. et al., "Intraoperative tissue identification using rapid evaporative ionization mass spectrometry", Science Trans Medicine, 5(194):194ra93, 2013.
(Continued)

*Primary Examiner* — Nicole M Ippolito
(74) *Attorney, Agent, or Firm* — Stephen J. Scribner

(57) ABSTRACT

In a method for spatially localizing mass-spectrometry analysis of an analyte derived from an energy event, an electrical device is used to deliver an energy event to a substrate, and the analyte produced is analyzed using mass spectrometry. Electrical signals sent to and received from the electrical device under different modes of operation are sensed and classified according to each different mode of operation. A location of the electrical device is tracked in three dimensions during the energy event, and a processor is used to perform spatial-temporal alignment of the mass-spectrometry, the determined modes of operation of the electrical device, and the tracked location of the electrical device, wherein mass spectrometry data corresponding to the determined modes of the electrical device are identified and localized within the site of the energy event. The substrate may be tissue in a surgical site, and the electrical device may be an electrocautery device.

17 Claims, 3 Drawing Sheets

(51) Int. Cl.
  *A61B 5/145* (2006.01)
  *A61B 18/00* (2006.01)
(52) U.S. Cl.
  CPC ........ *H01J 49/0004* (2013.01); *H01J 49/164* (2013.01); *A61B 2018/00607* (2013.01); *A61B 2018/00773* (2013.01)
(58) Field of Classification Search
  USPC ........................................ 250/281, 282, 288
  See application file for complete search history.

(56) References Cited

OTHER PUBLICATIONS

Asselin, M, et al., Navigated real-time molecular analysis in the operating theatre, demonstration of concept. SPIE Medical Imaging, 109512C, 2019.

* cited by examiner

SPATIO-TEMPORAL LOCALIZATION FOR MASS SPECTROMETRY SAMPLE ANALYSIS

RELATED APPLICATION

This application claims the benefit of the filing date of Application No. 62/864,137, filed on Jun. 20, 2019, the contents of which are incorporated herein by reference in their entirety.

FIELD

This invention relates to spatio-temporal localization of mass spectrometry sample analysis for products of an energy delivery event. Embodiments may be implemented in computer-assisted surgical procedures using electro-surgical devices for in vivo analysis and characterization of tissues.

BACKGROUND

In computer-assisted surgery, among other applications, situations arise when it is necessary to determine the status of tracked power tools in order to perform accurate spatial and/or temporal monitoring of the tool. This may involve the need to detect what is often referred to as an "energy event", when the power tool, such as an electrosurgical device, is being activated within tissue during surgery. A complicating factor is the need for an isolated sensing and feedback mechanism which does not interfere in any way with the clinically certified power tool.

One such electrosurgical device, an electrocautery tool, is used during surgery to cut tissue and to apply coagulation to the surgical site. The two main modes of the device that need to be distinguished are cut and coagulation. In coagulation mode, the device induces a gradual temperature rise in the cells which causes the cells to dehydrate and shrink without bursting. This is particularly useful to seal minor blood vessels. The cut mode causes a more rapid heating of the tissue which results in the cellular water boiling and causes the cells to rupture, which is most useful to separate tissue while also sealing minor vasculature.

Precise knowledge of the electrocautery mode is critical for spatially-navigated metabolomic analysis of the surgical aerosol, simply known as "smoke". Rapid evaporative ionization mass spectrometry (REIMS) has been shown to have good sensitivity and specificity in metabolomic tissue identification [1]. However, a major challenge for spatially-navigated mass spectrometry tissue characterization is precise compensation for the time delay caused by the propagation of the surgical smoke from the surgical site to the mass spectrometer.

SUMMARY

According to one aspect of the invention there is provided a method for spatially localizing mass-spectrometry analysis of an analyte derived from an energy event, comprising: using an electrical device to deliver an energy event to a substrate; desorbing analyte for analysis from a site of the energy event; analyzing the analyte using mass spectrometry; non-invasively sensing electrical signals sent to and received from the electrical device under different modes of operation; classifying the electrical signals according to each different mode of operation; tracking a location of the electrical device in three dimensions during the energy event; using a processor to perform spatial-temporal alignment of the mass-spectrometry, the determined modes of operation of the electrical device, and the tracked location of the electrical device; wherein mass spectrometry data corresponding to the determined modes of the electrical device are identified and localized within the site of the energy event.

In one embodiment, the site of the energy event is a surgical site.

In one embodiment, the electrical device is an electrocautery device.

In one embodiment, the analyte is generated from native tissues at the surgical site.

In one embodiment, wherein the analyte comprises smoke.

In one embodiment, the different modes of operation of the electrocautery device comprise: cut in air; coagulation in air; cut in tissue; and coagulation in tissue.

In one embodiment, the mass spectrometry is rapid evaporative ionization mass spectrometry (REIMS).

In one embodiment, the 3-D tracking is selected from optical tracking, electromagnetic tracking, and a combination thereof.

According to another aspect of the invention there is provided apparatus for carrying out any of the methods described herein.

In one embodiment, as apparatus for spatially localizing mass-spectrometry analysis of an analyte derived from an energy event comprises: an electrical device that delivers an energy event to a substrate; a system that transfers analyte from a site of the energy event for analysis by mass spectrometry; non-invasive sensors that sense electrical signals sent to and received from the electrical device under different modes of operation; a processor that classifies the electrical signals according to each different mode of operation; a tracker that tracks a location of the electrical device in three dimensions during the energy event; wherein the processor performs spatial-temporal alignment of the mass-spectrometry, the determined modes of operation of the electrical device, and the tracked location of the electrical device; wherein mass spectrometry data corresponding to the determined modes of the electrical device are identified and localized within the site of the energy event.

BRIEF DESCRIPTION OF THE DRAWINGS

For a greater understanding of the invention, and to show more clearly how it may be carried into effect, embodiments will be described, by way of example, with reference to the accompanying drawings, wherein.

DETAILED DESCRIPTION OF EMBODIMENTS

Methods described herein may be used in any application where an electrical device may be used to deliver an energy event to a substrate to generate an analyte material, the analyte material is characterized using mass spectrometry, and there is a need to localize the mass spectrometry data within a location of the energy event in/on the substrate. The methods described herein may be applied to any electrical or electrically controlled device used to generate the analyte as an aerosol, where a sampling/analyzing technique involves transferring analyte material from a site of the energy event through a sampling or transfer system where there is a need to compensate for delay associated with transit of the analyte material through the sampling or transfer system. Embodiments are described herein with respect to surgical applications, however, the invention is not limited thereto.

For example, as mentioned above, a major challenge for spatially-navigated mass spectrometry tissue characterization using electrocautery is precise compensation for the time delay caused by the propagation of the aerosol (i.e., smoke) from the surgical site to the mass spectrometer. The time delay is variable, owing to the varying length and curvature of the smoke evacuation tubing. In order to accurately resolve the variable time delay, one can temporally analyze the electrocautery burn, including the beginning and end of each cutting or coagulation action. Having captured the tracking data during the time period of the burn, the mass-spectra can be mapped to their spatial locations [2]. However, there are limitations with such an approach as the intra-operative state of the electrocautery cannot be accurately determined.

Although embodiments are described herein with respect to rapid evaporative ionization mass spectrometry (REIMS), it will be appreciated that the methods described herein are not limited thereto, and may be extended to other ionization methods such as desorption electrospray ionization (DESI), matrix-assisted laser desorption ionization (MALDI), and laser description ionization (LDI). The methods described herein may find utility in any application where it is desired to determine the transit time of analyte material through a sampling or transfer tube interface between a sample and an ion analysis instrument. The methods described herein may be suitable for any ambient ionization process, or with any ambient ionization ion source, such as those described below.

According to various embodiments an electrical device is used to generate an aerosol, smoke, or vapour from one or more regions of a substrate (e.g., tissue). In the particular embodiments described, the electrical device is an electrosurgical device such as a surgical electrocautery tool. In general, the electrical device may comprise an ambient ionization ion source which is characterized by the ability to generate analyte aerosol, smoke, or vapour from the substrate without the requirement to add a matrix or a reagent to the substrate, which would prevent the ability to perform in vivo analysis of tissue and also, more generally, prevent the ability to provide a rapid simple analysis of substrate material. Therefore, electrical devices used to produce ambient ionization of a substrate are advantageous since they do not require the addition of a matrix or a reagent (and hence are suitable for analysis of in vivo tissue) and since they enable a rapid simple analysis of substrate material to be performed.

Various ambient ionization techniques are known and fall within the scope of the invention. Ambient ionization techniques differ in their ionization method but all generate gas-phase ions directly from native (i.e., untreated or unmodified) samples, and therefore they do not require any sample preparation. As a result, the various ambient ionization techniques enable both in vivo and ex vivo tissue samples to be analyzed without necessitating the time and expense of adding a matrix or reagent to the tissue sample or other target material.

An exemplary embodiment will now be described. This embodiment provides a practical method for robust and accurate identification of the intra-operative state of an electrocautery tool, and enables navigated intra-operative analysis and characterization of tissue using mass spectrometry, particularly REIMS, as the ambient ionization technique to analyze the smoke produced.

FIG. 1 is a diagram of the set-up, according to one embodiment. Referring to FIG. 1, the set-up included an electrocautery tool (i.e., "surgical pencil") 102 which received its driving current from an electrosurgical generator 104, and a return electrode 106. A tracking marker 108 disposed on electrocautery tool 102 interfaced with a tracker 110 provided tracking data 112 for surgical navigation. It is noted that optical or electromagnetic tracking may be used. Current sensors (e.g., SCT-013; Beijing YaoHuadechang Electronic Co., Ltd., Beijing, CN) 114, 116 were provided on the live and return electrodes, respectively, of the electrocautery tool. The current sensors were connected to a digital oscilloscope (PicoScope P2204A USB oscilloscope; Pico Technology, St Neots, UK). The oscilloscope amplified and digitized the waveforms obtained from the current sensors of the electrocautery tool 102, and provided output 120 for analysis. In other embodiments, the electrocautery current sensor signals may be processed using other signal processing apparatus. Smoke from the electrocautery tool 102 was directed via tubing to a REIMS machine 122 which provided mass spectrometry data 124.

In one embodiment, current data from the oscilloscope were streamed via PLUS Toolkit [3] to SlicerIGT surgical navigation platform [4]. Current signal wave analysis was performed in MATLAB (The MathWorks, Inc., Natick, Mass., USA), which was bridged in real-time to SlicerIGT where the mass-spectra were mapped to their spatial locations.

Determining the electrocautery modes (burn, coagulation, as well as whether the electrocautery tool was in contact with tissue or not) serves a double purpose in the embodiments. Firstly, the mass spectra differ slightly between cut and coagulation modes, so these different diathermy modes must be distinguished. The electrical signals sensed from the electrocautery tool were used to differentiate between these modes. To improve tissue analysis accuracy, machine-learned models trained on data-specific to each electrocautery mode in real-time may be used. Secondly, classifying when the electrocautery tool is activated in the air versus when it is being applied to tissue allows detection of the precise beginning and end of an electrocautery burn. The air/tissue classification is necessary because surgeons often activate the electrocautery tool before it is in contact with the tissue.

To ensure generality and robustness for electrocautery mode detection, experiments were conducted with electrosurgical generators from two different manufacturers: the Erbe VIO 50 C (Erbe Elektromedizin GmbH, Tuebingen, Germany) and the Valleylab Force FX C (Avante Health Solutions, Illinois, USA). For each generator, the electrical profile of five "burns" in each of four modes were recorded. The four modes were "cut" in air and tissue, and "coagulation" in air and tissue. For the experiments, bovine tissue was used. The experiments were repeated three times collecting samples with temporal resolutions of 20 μs/division, 200 μs/division and 20 ms/division. Exemplary signals from the oscilloscope are shown in FIGS. 2A-2F. These data were labelled according to the four modes: cut-air, coag-air, cut-tissue, and coag-tissue, and were clustered based on selected features. In this embodiment the features were the magnitude of the live electrode signal, the magnitude of the return electrode signal, and the magnitude of the difference between them, although other features could be used. A processor was used to perform classification according to an algorithm that computed the distance between an unlabelled signal and the centroids of the clusters. Misclassified signals may be rectified by low-pass filtering since surgeons usually do not switch electrocautery mode within a single burn.

Figure 1:
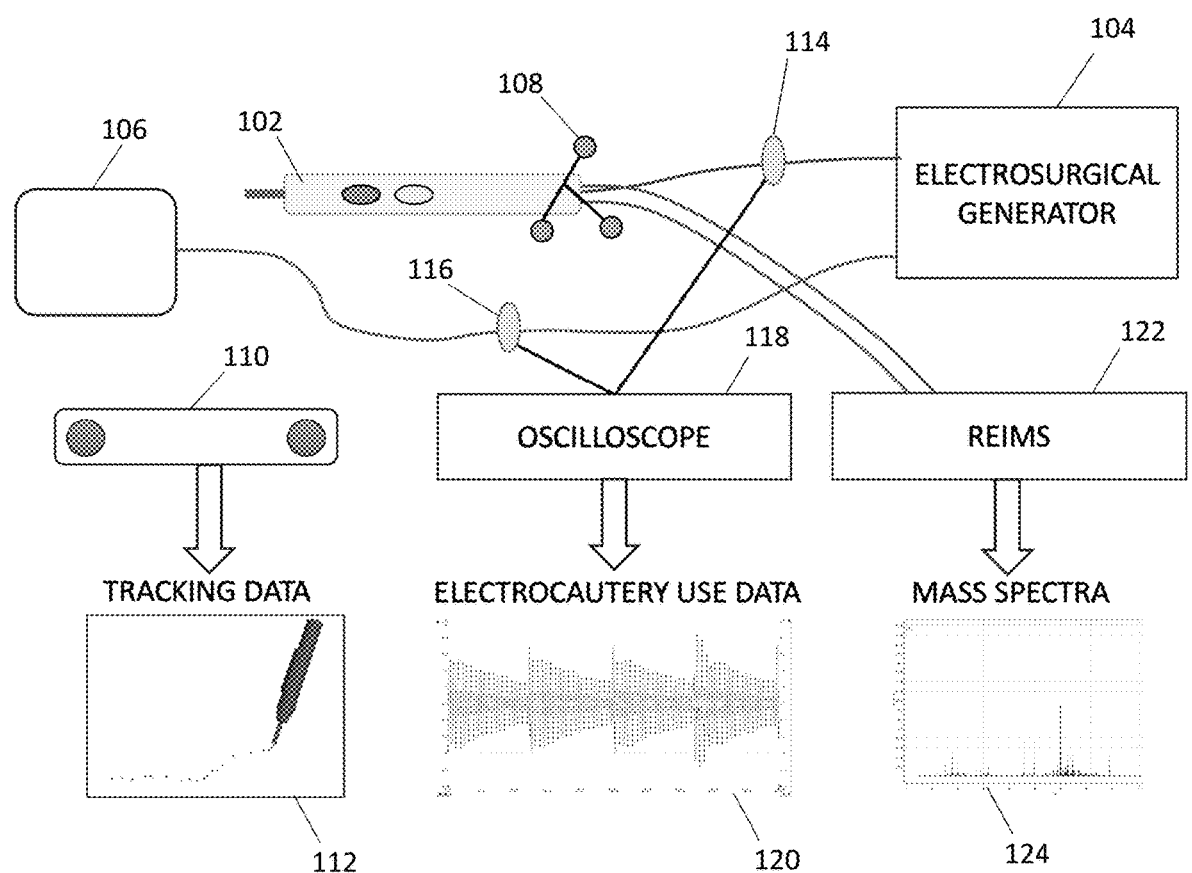
FIG. 1 is a schematic diagram of a set-up for intra-operative time-delay compensation for spatially localized mass spectrometry tissue analysis, according to an embodiment.
Figure 2A:
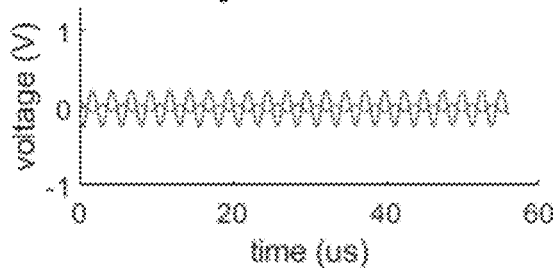
FIGS. 2A-2F are plots showing representative electrical signals of an electrocautery tool in cut and coagulation modes in air and in tissue.
Figure 2B:
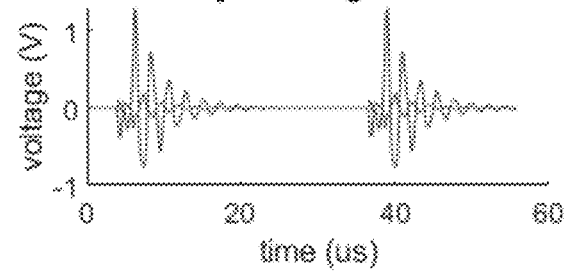
Figure 2C:
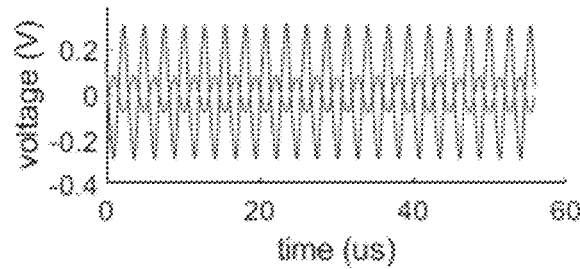
Figure 2D:
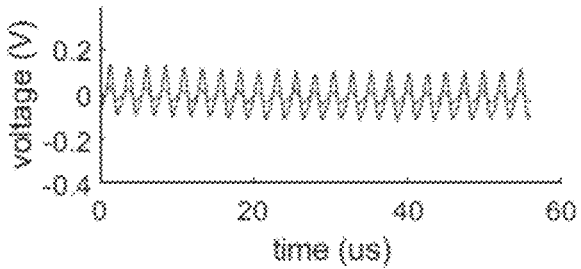
Figure 2E:
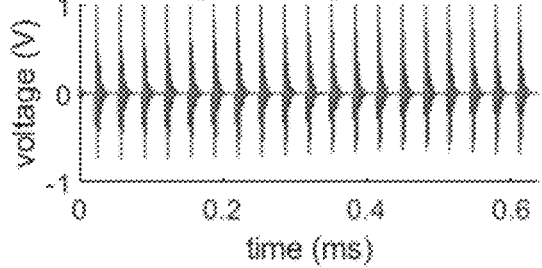
Figure 2F:
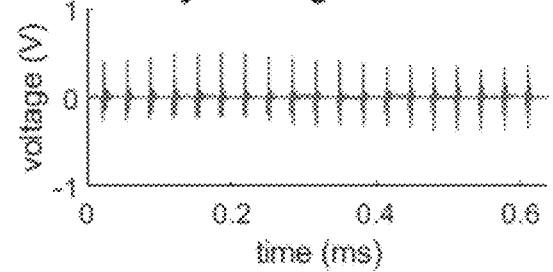
Figure 3:
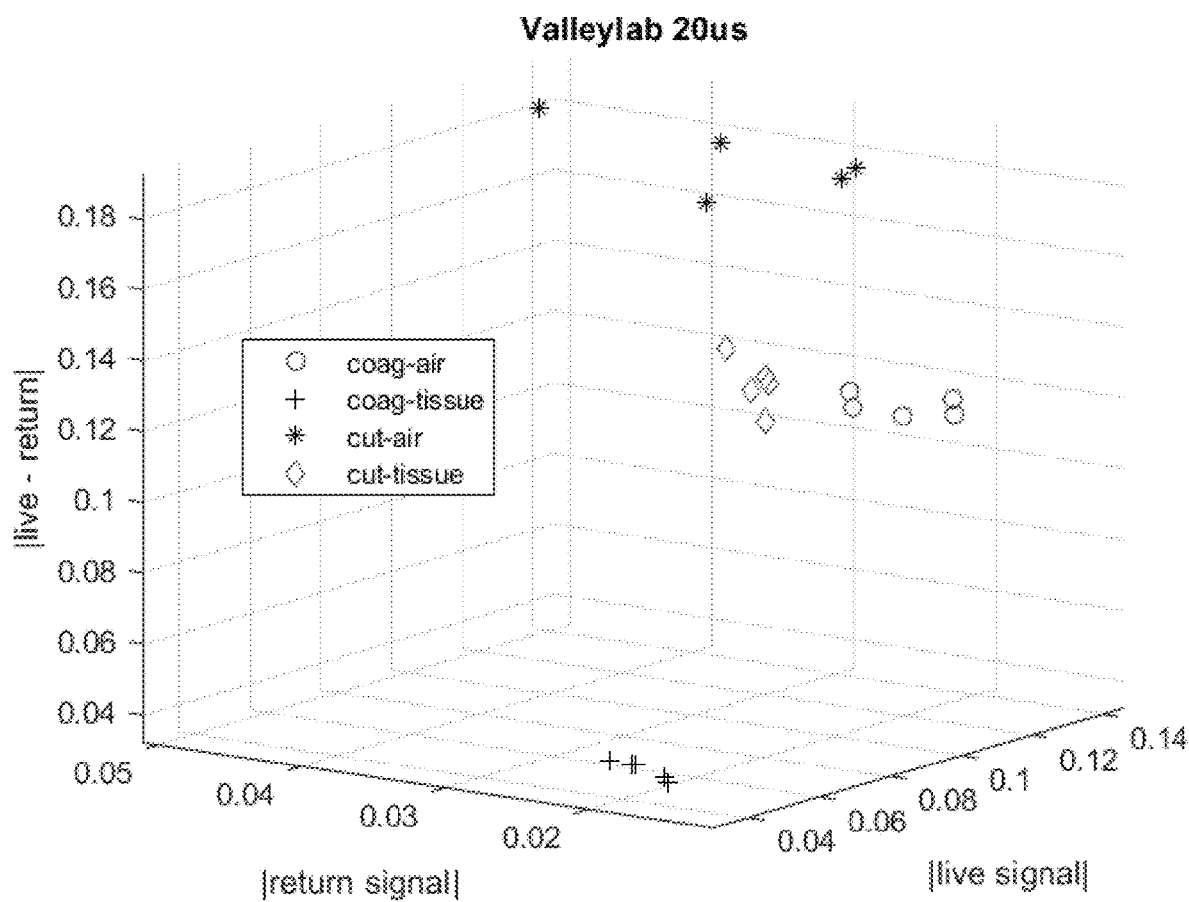
FIG. 3 is a 3-D plot showing a clustering of sample of electrical signals of an electrocautery tool in four modes of operation.

FIGS. 2A-2F show representative signals captured from the two different electrosurgical generators. It can be see that there are differences between cut and coagulation modes (FIGS. 2A and 2B), and there is a subtle low-frequency sinusoid present only in the envelope of cut-tissue signals (FIG. 2D). FIG. 3 is a plot of the clustered signals using data from the Valleylab electrosurgical generator at 20 μs/division resolution. The plot shows clear separation and identification of the four electrocautery modes. For each generator there was a "preferred" resolution for which the signals were clustered better than other resolutions. Thus, one embodiment may include trying multiple resolutions (this can be done quickly as only about 1 second is needed to acquire sufficient data) to identity a suitable resolution for use in surgery. It is of note that the training and classification model selected was relatively straight-forward to implement, and thus is well-suited to any retraining that might be necessary. Other embodiments may include, for example, machine learning to identify the cautery state.

For example, retraining may be necessary if a different electrocautery generator is used, or when one or more electrical parameters (e.g., voltage, current, frequency, waveform) for the electrocautery tool are changed significantly. The model can be updated with no disruption to the surgical workflow by processing additional cautery activations. For example, one or more cut-air and coag-air samples of the electrical signals may be obtained, and then tissue cuts may be labelled using visible feedback from the surgical scene and the electrocautery generator. Such recalibration and retraining, if necessary, may be done seamlessly using only a few cutting and coagulation events at the beginning of the surgery, such as upon skin incision when tissue characterization is not yet necessary.

For meaningful spatio-temporal localization, the method should be faster than the shortest time delay between the electrocautery action and the appearance of mass spectra. This time delay is typically never shorter than one second [1], [2] which is readily attainable in the exemplary system described herein. Classification of the modes of the electrocautery device according to the embodiments described herein is robust, and enables accurate spatio-temporal alignment of mass spectrometry when integrated with 3-D tracking of the electrocautery device.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] Balog J, et al., Intraoperative tissue identification using rapid evaporative ionization mass spectrometry. Science Trans Medicine, 5(194):194ra93, 2013.

[2] Asselin, M, et al., Navigated real-time molecular analysis in the operating theatre, demonstration of concept. SPIE Medical Imaging, 109512C, 2019.

[3] Lasso, A, et al., PLUS: Open-source toolkit for ultrasound-guided intervention systems. IEEE Trans Biomed Eng, 61(10):2527-2537, 2014.

[4] Ungi, T., et al., Open-source platforms for navigated image-guided interventions. Med Image Anal, 33:181-186, 2016.

The invention claimed is:

1. A method for spatially localizing mass-spectrometry analysis of an analyte derived from an energy event, comprising:
   using an electrical device to deliver an energy event to a substrate;
   desorbing analyte for analysis from a site of the energy event;
   analyzing the analyte using mass spectrometry;
   non-invasively sensing electrical signals sent to and received from the electrical device under different modes of operation;
   classifying the electrical signals according to each different mode of operation;
   tracking a location of the electrical device in three dimensions during the energy event;
   using a processor to perform spatial-temporal alignment of the mass-spectrometry, the determined modes of operation of the electrical device, and the tracked location of the electrical device;
   wherein mass spectrometry data corresponding to the determined modes of the electrical device are identified and localized within the site of the energy event.

2. The method of claim 1, wherein the site of the energy event is a surgical site.

3. The method of claim 2, wherein the electrical device is an electrocautery device.

4. The method of claim 3, wherein the analyte comprises smoke.

5. The method of claim 3, wherein the different modes of operation of the electrocautery device comprise: cut in air; coagulation in air; cut in tissue; and coagulation in tissue.

6. The method of claim 2, wherein the analyte is generated from native tissues at the surgical site.

7. The method of claim 1, wherein the mass spectrometry is rapid evaporative ionization mass spectrometry (REIMS).

8. The method of claim 1, wherein the 3-D tracking is selected from optical tracking, electromagnetic tracking, and a combination thereof.

9. Apparatus for carrying out the method of claim 1.

10. Apparatus for spatially localizing mass-spectrometry analysis of an analyte derived from an energy event, comprising:
    an electrical device that delivers an energy event to a substrate;
    a system that transfers analyte from a site of the energy event for analysis by mass spectrometry;
    non-invasive sensors that sense electrical signals sent to and received from the electrical device under different modes of operation;
    a processor that classifies the electrical signals according to each different mode of operation;
    a tracker that tracks a location of the electrical device in three dimensions during the energy event;
    wherein the processor performs spatial-temporal alignment of the mass-spectrometry, the determined modes of operation of the electrical device, and the tracked location of the electrical device;

wherein mass spectrometry data corresponding to the determined modes of the electrical device are identified and localized within the site of the energy event.

11. The apparatus of claim 10, wherein the site of the energy event is a surgical site.

12. The apparatus of claim 11, wherein the electrical device is an electrocautery device.

13. The apparatus of claim 12, wherein the analyte comprises smoke.

14. The apparatus of claim 12, wherein the different modes of operation of the electrocautery device comprise: cut in air; coagulation in air; cut in tissue; and coagulation in tissue.

15. The apparatus of claim 11, wherein the analyte is generated from native tissues at the surgical site.

16. The apparatus of claim 10, wherein the mass spectrometry is rapid evaporative ionization mass spectrometry (REIMS).

17. The apparatus of claim 10, wherein the 3-D tracking is selected from optical tracking, electromagnetic tracking, and a combination thereof.

\* \* \* \* \*